(12) United States Patent
Lopez de Leon et al.

(10) Patent No.: US 8,975,059 B2
(45) Date of Patent: Mar. 10, 2015

(54) POLYPEPTIDES HAVING ENDOGLUCANASE ACTIVITY AND POLYNUCLEOTIDES ENCODING SAME

(71) Applicant: Novozymes A/S, Bagsvaerd (DK)

(72) Inventors: Alfredo Lopez de Leon, Davis, CA (US); Michael Rey, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 42 days.

(21) Appl. No.: 13/912,915

(22) Filed: Jun. 7, 2013

(65) Prior Publication Data

US 2013/0291230 A1    Oct. 31, 2013

Related U.S. Application Data

(62) Division of application No. 13/600,071, filed on Aug. 30, 2012, now Pat. No. 8,465,958, which is a division of application No. 12/763,578, filed on Apr. 20, 2010, now Pat. No. 8,268,606, which is a division of application No. 12/327,509, filed on Dec. 3, 2008, now Pat. No. 7,741,074.

(60) Provisional application No. 60/992,576, filed on Dec. 5, 2007.

(51) Int. Cl.
| | | |
|---|---|---|
| C12N 9/42 | (2006.01) |
| C12N 9/24 | (2006.01) |
| C12N 1/20 | (2006.01) |
| C12N 1/00 | (2006.01) |
| C12N 15/00 | (2006.01) |
| C12P 21/06 | (2006.01) |
| C12P 19/34 | (2006.01) |
| C12N 5/10 | (2006.01) |
| C07H 21/04 | (2006.01) |
| C07K 1/00 | (2006.01) |
| A01H 5/00 | (2006.01) |
| C12N 15/87 | (2006.01) |
| C12N 15/82 | (2006.01) |
| C12P 19/14 | (2006.01) |

(52) U.S. Cl.
CPC .............. *C12N 9/42* (2013.01); *C12N 15/8246* (2013.01); *C12P 19/14* (2013.01); *C12N 9/2437* (2013.01); *C12Y 302/01004* (2013.01); *Y02E 50/16* (2013.01)
USPC ......... 435/209; 435/200; 435/69.1; 435/91.1; 435/320.1; 435/252.3; 435/252.31; 435/252.33; 435/254.11; 435/254.21; 435/254.22; 435/254.23; 435/254.4; 435/254.6; 536/23.1; 536/23.2; 530/350; 800/298; 800/278

(58) Field of Classification Search
USPC ......... 435/209, 200, 69.1, 91.1, 320.1, 252.3, 435/252.33, 254.11, 254.21, 254.22, 435/254.23, 254.4, 254.5, 254.6, 419; 536/23.1, 23.2; 530/350; 800/298, 278
See application file for complete search history.

(56) References Cited

FOREIGN PATENT DOCUMENTS

| WO | 2005074647 | 8/2005 |
| WO | 2007115201 | 10/2007 |

OTHER PUBLICATIONS

Breuil et al., Biotechnology Letters, vol. 8, 1986, pp. 673-676.
(Continued)

*Primary Examiner* — Ganapathirama Raghu
(74) *Attorney, Agent, or Firm* — Eric J. Fechter

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods of producing and using the polypeptides.

20 Claims, 5 Drawing Sheets

(56) References Cited

OTHER PUBLICATIONS

Kvesitadze et al., Applied Biochemistry and Biotechnology, vol. 50, 1995, pp. 137-144.
Gilbert et al., Bioresource Technology, vol. 39, 1992, pp. 147-154.
Guo et al, 2004, Proc Natl Acad Sci USA 101(25), 9205-9210.
Kisselev et al, 2002, Structure 10, 8-9.
Seffernick et al, 2001, J Bacteriol 183(8), 2405-2410.
Wishart et al, 1995, J Biol Chem 270(45), 26782-26785.
Witowski et al, 1999, Biochemistry 38, 11643-11650.

```
          M   A   S   S   I   V   R   L   G   A   A   A   A   L   A   Y   G   S   G   A
1     ATGGCCTCCTCCATCGTCCGGCTGGGCGCCGCGGCTGCCCTAGCCTACGGCTCCGGTGCT
          A   A   L   Q   S   Y   Q   L   S   E   S   Y   N   P   T   N   F   F   D   K
61    GCCGCCCTCCAGTCCTACCAACTCTCGGAGTCATACAACCCCACCAACTTCTTTGACAAG
          F   N   F   F   D   G   K   D   P   N   S   G   F   V   Q   Y   R   N   R   T
121   TTCAACTTCTTCGATGGCAAGGACCCCAACAGTGGATTCGTTCAGTACAGAAACAGAACC
          Y   A   S   S   H   G   L   I   Q   T   G   T   N   D   V   T   I   R   V   D
181   TACGCCAGCTCCCATGGCCTCATCCAGACGGGGACCAACGACGTGACCATCCGCGTCGAT
          T   T   G   T   D   Q   N   G   R   S   S   V   R   L   E   S   I   N   T   Y
241   ACGACCGGCACCGACCAGAACGGACGCAGCAGCGTCCGGCTGGAGAGTATCAACACGTAC
          N   S   G   L   F   I   A   D   F   T   H   L   P   Y   A   P   C   G   A   W
301   AATTCGGGCCTGTTCATCGCCGATTTCACCCACCTGCCCTACGCTCCCTGTGGTGCTTGG
          P   A   F   W   M   V   G   P   N   W   P   T   D   G   E   I   D   I   Y   E
361   CCAGCCTTCTGGATGGTGGGCCCCAACTGGCCCACGGATGGCGAGATCGACATCTACGAG
          G   W   N   L   A   P   T   N   K   V   V   L   H   T   D   S   P   T   I   S
421   GGCTGGAACCTGGCCCCGACGAACAAGGTTGTGCTGCACACGGATAGCCCGACCATCTCG
          G   T   C   R   I   Q   Q   G   D   F   T   G   T   L   E   Y   P   D   C   W
481   GGCACGTGCCGGATCCAGCAGGGCGACTTCACTGGCACCCTGGAGTACCCCGACTGCTGG
          T   N   D   P   T   Q   P   S   N   A   G   C   A   V   E   E   K   N   G   L
541   ACCAACGACCCCACCCAGCCCAGCAATGCGGGTTGTGCCGTTGAGGAGAAGAACGGCCTG
          F   G   N   A   A   G   G   V   Y   A   T   E   W   Q   E   D   S   I   K   V
601   TTCGGGAATGCCGCCGGCGGCGTCTACGCTACCGAGTGGCAGGAAGACAGCATCAAGGTC
          W   S   W   S   H   N   S   V   P   A   D   V   T   S   G   K   P   N   P   A
661   TGGAGCTGGTCTCATAACAGCGTCCCCGCTGATGTCACGAGTGGCAAACCCAACCCGGCG
          N   W   G   K   P   T   L   A   A   G   S   Q   C   D   V   K   S   A   F   R
721   AACTGGGGTAAGCCCACTCTCGCCGCGGGCAGCCAGTGCGATGTCAAGTCGGCATTCCGC
          D   M   R   L   I   L   N   I   N   F   C   G   D   A   A   G   N   T   W   P
781   GACATGCGCTTGATCCTGAATATCAACTTCTGCGGTGACGCTGCCGGCAACACCTGGCCC
          G   S   A   C   Q   K   S   T   N   V   P   A   C   Y   T   Y   V   Q   W   N
841   GGATCTGCGTGCCAGAAGAGTACCAATGTCCCCGCGTGCTATACCTACGTGCAGTGGAAC
          P   H   V   Y   N   S   T   F   W   S   V   R   S   I   K   V   Y   Q   L   G
901   CCGCACGTCTACAACAGCACGTTCTGGTCCGTCCGGAGCATCAAGGTGTACCAGCTCGGG
          E   S   Q   T   T   T   T   T   R   S   S   T   S   T   T   T   S   T   R
961   GAGTCGCAGACCACGACCACCACGACCAGGTCCTCGACTTCGACTACGACGTCGACCAGG
          S   S   T   S   T   T   T   S   A   R   S   S   T   S   T   T   T   S   A   R
1021  TCCTCGACTTCGACTACGACGTCGGCCAGGTCCTCGACTTCGACCACGACGTCGGCCAGG
          S   S   T   S   T   T   T   T   S   L   T   S   T   T   S   S   I   S   T   T
1081  TCCTCGACTTCGACCACGACTACCTCTTTGACTTCGACCACGTCTTCAATTTCGACCACG
          T   T   S   S   T   S   T   S   T   S   T   A   S   P   T   S   T   S   T   S
1141  ACCACGTCCTCGACCTCGACCAGCACGTCGACGGCGTCCCCCACCTCCACGTCTACCAGC
          T   S   A   A   V   T   S   A   I   T   S   E   T   A   T   A   T   A   T   E
1201  ACCTCGGCCGCTGTGACCTCGGCCATCACTTCAGAGACTGCCACGGCGACTGCCACGGAG
          T   A   T   E   T   E   S   D   C   P   D   D   N   A   T   S   T   T   T   G
1261  ACCGCCACGGAGACCGAGAGCGACTGCCCTGATGACAACGCCACCTCCACCACGACCGGT
          A   A   T   T   E   T   G   S   S   T   S   T   T   A   T   A   T   A   T   E
```

Fig. 1A

```
1321  GCTGCCACCACGGAGACTGGGTCGAGCACAAGCACGACGGCTACCGCGACTGCCACTGAG
       T  E  S  D  C  P  D  D  N  A  T  S  T  T  T  G  A  A  T  T
1381  ACCGAGAGCGACTGCCCTGACGACAACGCCACCTCCACCACGACCGGTGCTGCCACCACG
       E  T  G  S  S  T  T  A  T  A  T  E  T  E  S  D  C  P
1441  GAGACTGGGTCAAGCACGACGGCTACCGCGACTGCCACTGAGACCGAGAGCGACTGCCCC
       D  D  N  A  T  S  T  T  T  G  A  A  T  T  E  T  G  S  S  T
1501  GATGACAACGCCACCTCCACCACGACCGGTGCTGCCACCACGGAGACTGGGTCGAGCACG
       T  A  T  A  T  G  T  A  A  P  S  S  S  V  P  D  V  T  D  I
1561  ACGGCTACCGCGACCGGGACCGCTGCGCCTTCCAGCTCGGTCCCCGACGTGACCGATATT
       V  T  A  T  A  T  G  G  F  T  T  S  T  I  Y  T  T  I
1621  GTCACTGCTACCGCGACCGCGACCGGAGGCTTCACCACGTCGACCATTTACACCACGATC
       T  S  T  I  T  S  C  A  P  T  V  T  N  C  P  A  R  T  V  T
1681  ACGTCGACCATTACGTCGTGCGCGCCGACCGTGACCAACTGCCCCGCGCGCACCGTTACG
       S  V  I  P  I  G  T  T  V  C  P  V  T  E  A  S  S  A  P  V
1741  TCGGTCATCCCCATCGGCACGACCGTCTGCCCCGTGACCGAGGCCAGCTCGGCGCCGGTG
       T  T  E  T  A  T  L  P  E  G  W  T  T  S  T  V  Y  S  T  I
1801  ACGACGGAGACGGCCACCCTGCCGGAGGGCTGGACCACGTCGACCGTCTACTCCACCATC
       T  Y  T  I  T  S  C  A  A  S  V  T  N  C  P  A  R  V  T  T
1861  ACGTACACGATCACGTCGTGCGCGGCGTCGGTCACCAACTGCCCCGGCCCGCGTGACCACG
       S  V  V  A  V  G  T  T  V  C  P  I  A  S  F  S  A  S  P  S
1921  TCGGTGGTTGCCGTCGGCACCACCGTCTGCCCGATCGCGTCGTTCAGCGCCAGCCCCAGC
       T  S  A  G  V  N  P  S  E  V  V  S  T  V  R  S  F  T  T  V
1981  ACCAGCGCCGGCGTCAACCCCAGCGAGGTCGTCAGCACGGTGCGCTCCTTCACCACCGTC
       S  K  T  T  V  V  L  P  R  S  G  S  A  A  G  S  S
2041  TCCAAGACGACGACCGTCGTGCTGCCCCGCCCCAGCGGGTCGGCCGCCGGGTCGTCGTCA
       S  P  V  L  V  A  S  P  G  P  L  L  L  R  R  L  L  S  R  L
2101  TCGCCGGTCCTCGTCGCCAGCCCGGGCCCCCTCCTCCTCCGCCGGCTCCTCTCCCGCCTC
       P  L  R  A  E  R  G  G  R  W  Q  Q  R  H  R  L  R  A  A  G
2161  CCCCTCCGTGCCGAGCGTGGTGGTCGGTGGCAACAACGGCACCGCCTCCGTGCCGCCGGT
       P  G  R  Y  R  Q  P  A  G  R  Q  H  Q  P  V  A  A  G  D  C
2221  CCAGGTCGTTACCGCCAGCCAGCCGGGCGCCAGCACCAGCCTGTCGCAGCCGGTGACTGC
       R  R  R  P  H  D  G  G  Q  R  A  D  G  A  A  A  W  C  G  R
2281  CGGCGGCGGCCGCATGATGGCGGGCAGCGGGCTGATGGCGCTGCTGCTTGGTGCGGCCGC
       G  D  V  D  L  R  C  V  A  V  A  C  L  R  G  W  V  *
2341  GGCGATGTTGATCTAAGGTGTGTTGCTGTTGCTTGCTTGCGGGGGTGGGTGTAG
```

Fig. 1B

```
            M   R   A   S   S   L   T   A   L   S   F   F   S   S   L   V   A   A   L   P
  1     ATGCGTGCCAGCAGCCTCACCGCGCTGTCCTTCTTTTCGTCCCTTGTTGCGGCTCTCCCG
            A   P   A   Y   P   G   Y   T   L   L   W   S   D   E   F   A   G   P   A   G
 61     GCCCCAGCCTACCCGGGATACACACTCCTCTGGTCCGATGAATTCGCGGGCCCCGCCGGC
            S   S   P   D   Q   S   R   W   N   I   I   T   N   V   H   T   N   H   E   V
121     TCGAGCCCCGACCAGAGCCGCTGGAACATCATCACCAATGTCCACACCAACCACGAGGTC
            E   T   Y   T   T   S   N   Q   N   L   Q   I   S   G   G   G   T   V   Q   I
181     GAGACCTACACCACGTCGAACCAAAACCTCCAGATCTCCGGCGGCGGCACCGTCCAGATC
            V   P   R   K   S   P   S   G   Q   W   T   S   A   R   I   E   S   K   A   T
241     GTCCCGCGCAAGAGCCCCTCGGGGCAGTGGACGTCGGCGCGCATCGAGTCCAAGGCGACC
            F   T   P   A   A   G   K   V   T   M   F   E   A   A   I   R   F   G   T   N
301     TTCACCCCCGCCGCGGGCAAGGTGACCATGTTCGAGGCGGCGATCCGGTTCGGCACGAAC
            P   A   S   Q   K   Q   G   I   W   P   A   F   W   L   L   G   D   A   I   H
361     CCGGCGTCGCAGAAGCAGGGCATCTGGCCGGCGTTCTGGCTGCTGGGCGACGCGATCCAC
            H   G   T   A   W   P   L   C   G   E   L   D   I   M   E   T   V   N   G   L
421     CACGGCACCGCCTGGCCGCTGTGCGGCGAGCTCGACATCATGGAGACCGTCAACGGCCTG
            P   T   G   H   G   T   L   H   C   G   A   T   T   S   G   G   P   C   A   E
481     CCGACCGGCCACGGCACCCTGCACTGCGGCGCCACCACCAGCGGCGGGCCCTGCGCCGAG
            P   T   G   R   T   G   A   V   A   L   P   D   D   G   W   H   T   W   S   L
541     CCCACCGGCCGCACCGGCGCCGTCGCCCTGCCCGACGACGGCTGGCACACCTGGTCGCTG
            Q   I   D   R   T   N   A   A   G   G   W   A   G   E   V   I   K   F   L   K
601     CAAATCGACCGCACGAATGCCGCCGGCGGCTGGGCCGGCGAGGTCATCAAGTTCCTCAAG
            D   G   Q   V   F   F   Q   V   S   G   A   Q   L   G   D   E   G   I   W   A
661     GACGGCCAGGTGTTTTTCCAGGTCTCCGGCGCGCAGCTCGGGGACGAGGGCATCTGGGCC
            T   L   A   H   S   P   L   F   I   I   L   N   V   A   V   G   G   D   W   P
721     ACCCTCGCGCACTCGCCGCTGTTTATCATCTTGAACGTGGCGGTTGGCGGTGACTGGCCT
            G   A   P   N   A   A   T   A   D   G   Y   G   S   M   M   E   V   E   Y   V
781     GGTGCTCCCAACGCCGCGACTGCGGACGGCTACGGCAGTATGATGGAGGTCGAGTACGTC
            A   V   Y   S   S   *
841     GCCGTCTACTCGTCGTAA
```

Fig. 2

```
SEQUENCE LISTING

<160> NUMBER OF SEQ ID NOS: 8

<210> SEQ ID NO 1
<211> LENGTH: 2394
<212> TYPE: DNA
<213> ORGANISM: Thielavia terrestris

<400> SEQUENCE: 1
atggcctcct ccatcgtccg gctgggcgcc gcggctgccc tagcctacgg ctccggtgct      60
gccgccctcc agtcctacca actctcggag tcatacaacc ccaccaactt ctttgacaag     120
ttcaacttct tcgatggcaa ggaccccaac agtggattcg ttcagtacag aaacagaacc     180
tacgccagct cccatggcct catccagacg gggaccaacg acgtgaccat ccgcgtcgat     240
acgaccggca ccgaccagaa cggacgcagc agcgtccggc tggagagtat caacacgtac     300
aattcgggcc tgttcatcgc cgatttcacc cacctgccct acgctccctg tggtgcttgg     360
ccagccttct ggatggtggg ccccaactgg cccacggatg gcgagatcga catctacgag     420
ggctggaacc tggccccgac gaacaaggtt gtgctgcaca cggatagccc gaccatctcg     480
ggcacgtgcc ggatccagca gggcgacttc actggcaccc tggagtaccc cgactgctgg     540
accaacgacc cgacccagcc cagcaatgcg ggttgtgccg ttgaggagaa gaacggcctg     600
ttcgggaatg ccgccggcgg cgtctacgct accgagtggc aggaagacag catcaaggtc     660
tggagctggt ctcataacag cgtccccgct gatgtcacga gtggcaaacc caacccggcg     720
aactggggta agcccactct cgccgcgggc agccagtgcg atgtcaagtc ggcattccgc     780
gacatgcgct tgatcctgaa tatcaacttc tgcggtgacg ctgccggcaa cacctggccc     840
ggatctgcgt gccagaagag taccaatgtc cccgcgtgct ataacctacgt gcagtggaac     900 ccgcacgtct acaacagcac gttctggtcc gtccggagca tcaaggtgta ccagctcggg     960
gagtcgcaga ccacgaccac cacgaccagg tcctcgactt cgactacgac gtcgaccagg    1020
```

-continued

```
tcctcgactt cgactacgac gtcggccagg tcctcgactt cgaccacgac gtcggccagg    1080
tcctcgactt cgaccacgac tacctctttg acttcgacca cgtcttcaat ttcgaccacg    1140
accacgtcct cgacctcgac cagcacgtcg acggcgtccc ccacctccac gtctaccagc    1200
acctcggccg ctgtgacctc ggccatcact tcagagactg ccacggcgac tgccacggag    1260
accgccacgg agaccgagag cgactgccct gatgacaacg ccacctccac cacgaccggt    1320
gctgccacca cggagactgg gtcgagcaca agcacgacgg ctaccgcgac tgccactgag    1380
accgagagcg actgccctga cgacaacgcc acctccacca cgaccggtgc tgccaccacg    1440
gagactgggt caagcacgac ggctaccgcg actgccactg agaccgagag cgactgcccc    1500
gatgacaacg ccacctccac cacgaccggt gctgccacca cggagactgg gtcgagcacg    1560
acggctaccg cgaccgggac cgctgcgcct ccagctcgg tccccgacgt gaccgatatt    1620
gtcactgcta ccgcgaccgc gaccggaggc ttcaccacgt cgaccattta caccacgatc    1680
acgtcgacca ttacgtcgtg cgcgccgacc gtgaccaact gccccgcgcg caccgttacg    1740
tcggtcatcc ccatcggcac gaccgtctgc cccgtgaccg aggccagctc ggcgccggtg    1800
acgacggaga cggccaccct gccggagggc tggaccacgt cgaccgtcta ctccaccatc    1860
acgtacacga tcacgtcgtg cgcggcgtcg gtcaccaact gcccggcccg cgtgaccacg    1920
tcggtggttg ccgtcggcac caccgtctgc ccgatcgcgt cgttcagcgc cagccccagc    1980
accagcgccg gcgtcaaccc cagcgaggtc gtcagcacgg tgcgctcctt caccaccgtc    2040
tccaagacga cgaccgtcgt gctgccccgc ccagcgggt cggccgccgg gtcgtcgtca    2100
tcgccggtcc tcgtcgccag cccgggcccc ctcctcctcc gccggctcct ctcccgcctc    2160
cccctccgtg ccgagcgtgg tggtcggtgg caacaacggc accgcctccg tgccgccggt    2220
ccaggtcgtt accgccagcc agccgggcgc cagcaccagc tgtcgcagc cggtgactgc    2280 cggcggcggc cgcatgatgg cgggcagcgg gctgatggcg ctgctgcttg gtgcggccgc    2340
ggcgatgttg atctaaggtg tgttgctgtt gcttgcttgc gggggtgggt gtag          2394
```

<210> SEQ ID NO 2
<211> LENGTH: 797
<212> TYPE: PRT
<213> ORGANISM: Thielavia terrestris

<400> SEQUENCE: 2

```
Met Ala Ser Ser Ile Val Arg Leu Gly Ala Ala Ala Leu Ala Tyr
 1               5                  10                  15

Gly Ser Gly Ala Ala Leu Gln Ser Tyr Gln Leu Ser Glu Ser Tyr
            20                  25                  30

Asn Pro Thr Asn Phe Phe Asp Lys Phe Asn Phe Phe Asp Gly Lys Asp
        35                  40                  45

Pro Asn Ser Gly Phe Val Gln Tyr Arg Asn Arg Thr Tyr Ala Ser Ser
    50                  55                  60

His Gly Leu Ile Gln Thr Gly Thr Asn Asp Val Thr Ile Arg Val Asp
65                  70                  75                  80

Thr Thr Gly Thr Asp Gln Asn Gly Arg Ser Ser Val Arg Leu Glu Ser
                85                  90                  95

Ile Asn Thr Tyr Asn Ser Gly Leu Phe Ile Ala Asp Phe Thr His Leu
            100                 105                 110

Pro Tyr Ala Pro Cys Gly Ala Trp Pro Ala Phe Trp Met Val Gly Pro
        115                 120                 125

Asn Trp Pro Thr Asp Gly Glu Ile Asp Ile Tyr Glu Gly Trp Asn Leu
```

```
                    130                 135                 140
Ala Pro Thr Asn Lys Val Val Leu His Thr Asp Ser Pro Thr Ile Ser
145                 150                 155                 160

Gly Thr Cys Arg Ile Gln Gln Gly Asp Phe Thr Gly Thr Leu Glu Tyr
                165                 170                 175

Pro Asp Cys Trp Thr Asn Asp Pro Thr Gln Pro Ser Asn Ala Gly Cys
            180                 185                 190

Ala Val Glu Glu Lys Asn Gly Leu Phe Gly Asn Ala Ala Gly Gly Val
                195                 200                 205

Tyr Ala Thr Glu Trp Gln Glu Asp Ser Ile Lys Val Trp Ser Trp Ser
            210                 215                 220

His Asn Ser Val Pro Ala Asp Val Thr Ser Gly Lys Pro Asn Pro Ala
225                 230                 235                 240

Asn Trp Gly Lys Pro Thr Leu Ala Ala Gly Ser Gln Cys Asp Val Lys
                245                 250                 255

Ser Ala Phe Arg Asp Met Arg Leu Ile Leu Asn Ile Asn Phe Cys Gly
            260                 265                 270

Asp Ala Gly Asn Thr Trp Pro Gly Ser Ala Cys Gln Lys Ser Thr
            275                 280                 285

Asn Val Pro Ala Cys Tyr Thr Tyr Val Gln Trp Asn Pro His Val Tyr
            290                 295                 300

Asn Ser Thr Phe Trp Ser Val Arg Ser Ile Lys Val Tyr Gln Leu Gly
305                 310                 315                 320

Glu Ser Gln Thr Thr Thr Thr Thr Arg Ser Ser Thr Ser Thr Thr
                325                 330                 335

Thr Ser Thr Arg Ser Ser Thr Ser Thr Thr Ser Ala Arg Ser Ser
            340                 345                 350

Thr Ser Thr Thr Thr Ser Ala Arg Ser Ser Thr Ser Thr Thr Thr
            355                 360                 365

Ser Leu Thr Ser Thr Thr Ser Ser Ile Ser Thr Thr Thr Ser Ser
            370                 375                 380

Thr Ser Thr Ser Thr Ser Thr Ala Ser Pro Thr Ser Thr Ser Thr Ser
385                 390                 395                 400

Thr Ser Ala Ala Val Thr Ser Ala Ile Thr Ser Glu Thr Ala Thr Ala
                405                 410                 415

Thr Ala Thr Glu Thr Ala Thr Glu Thr Glu Ser Asp Cys Pro Asp Asp
                420                 425                 430

Asn Ala Thr Ser Thr Thr Thr Gly Ala Ala Thr Thr Glu Thr Gly Ser
            435                 440                 445

Ser Thr Ser Thr Thr Ala Thr Ala Thr Ala Glu Thr Glu Ser Asp
            450                 455                 460

Cys Pro Asp Asp Asn Ala Thr Ser Thr Thr Gly Ala Ala Thr
465                 470                 475                 480

Glu Thr Gly Ser Ser Thr Thr Ala Thr Ala Thr Ala Glu Thr Glu
                485                 490                 495

Ser Asp Cys Pro Asp Asp Asn Ala Thr Ser Thr Thr Gly Ala Ala
            500                 505                 510

Thr Thr Glu Thr Gly Ser Ser Thr Ala Thr Ala Gly Thr Ala
            515                 520                 525

Ala Pro Ser Ser Val Pro Asp Val Thr Asp Ile Val Thr Ala Thr
            530                 535                 540

Ala Thr Ala Thr Gly Gly Phe Thr Thr Ser Thr Ile Tyr Thr Thr Ile
545                 550                 555                 560
```

```
Thr Ser Thr Ile Thr Ser Cys Ala Pro Thr Val Asn Cys Pro Ala
            565                 570                 575

Arg Thr Val Thr Ser Val Ile Pro Ile Gly Thr Thr Val Cys Pro Val
        580                 585                 590

Thr Glu Ala Ser Ser Ala Pro Val Thr Thr Glu Thr Ala Thr Leu Pro
    595                 600                 605

Glu Gly Trp Thr Thr Ser Thr Val Tyr Ser Thr Ile Thr Tyr Thr Ile
610                 615                 620

Thr Ser Cys Ala Ala Ser Val Thr Asn Cys Pro Ala Arg Val Thr Thr
625                 630                 635                 640

Ser Val Val Ala Val Gly Thr Thr Val Cys Pro Ile Ala Ser Phe Ser
            645                 650                 655

Ala Ser Pro Ser Thr Ser Ala Gly Val Asn Pro Ser Glu Val Val Ser
            660                 665                 670

Thr Val Arg Ser Phe Thr Thr Val Ser Lys Thr Thr Thr Val Val Leu
        675                 680                 685

Pro Arg Pro Ser Gly Ser Ala Ala Gly Ser Ser Ser Pro Val Leu
690                 695                 700

Val Ala Ser Pro Gly Pro Leu Leu Arg Arg Leu Leu Ser Arg Leu
705                 710                 715                 720

Pro Leu Arg Ala Glu Arg Gly Gly Arg Trp Gln Gln Arg His Arg Leu
                725                 730                 735

Arg Ala Ala Gly Pro Gly Arg Tyr Arg Gln Pro Ala Gly Arg Gln His
            740                 745                 750

Gln Pro Val Ala Ala Gly Asp Cys Arg Arg Pro His Asp Gly Gly
        755                 760                 765

Gln Arg Ala Asp Gly Ala Ala Ala Trp Cys Gly Arg Gly Asp Val Asp
770                 775                 780

Leu Arg Cys Val Ala Val Ala Cys Leu Arg Gly Trp Val
785                 790                 795

<210> SEQ ID NO 3
<211> LENGTH: 858
<212> TYPE: DNA
<213> ORGANISM: Thielavia terrestris

<400> SEQUENCE: 3
atgcgtgcca gcagcctcac cgcgctgtcc ttcttttcgt cccttgttgc ggctctcccg      60
gccccagcct acccgggata cacactcctc tggtccgatg aattcgcggg ccccgccggc     120
tcgagccccg accagagccg ctggaacatc atcaccaatg tccacaccaa ccacgaggtc     180
gagacctaca ccacgtcgaa ccaaaacctc cagatctccg gcggcggcac cgtccagatc     240
gtcccgcgca agagcccctc ggggcagtgg acgtcggcgc gcatcgagtc caaggcgacc     300
ttcacccccg ccgcgggcaa ggtgaccatg ttcgaggcgg cgatccggtt cggcacgaac     360
ccggcgtcgc agaagcaggg catctggccg gcgttctggc tgctgggcga cgcgatccac     420
cacggcaccg cctggccgct gtgcggcgag ctcgacatca tggagaccgt caacggcctg     480
ccgaccggcc acggcaccct gcactgcggc gccaccacca cgcggcgggcc ctgcgccgag     540 cccaccggcc gcaccggcgc cgtcgccctg ccgacgacg ctggcacac ctggtcgctg       600 caaatcgacc gcacgaatgc cgccggcggc tgggccggcg aggtcatcaa gttcctcaag     660
gacggccagg tgttttttcca ggtctccggc gcgcagctcg gggacgaggg catctgggcc     720
accctcgcgc actcgccgct gtttatcatc ttgaacgtgg cggttggcgg tgactggcct     780
```

```
ggtgctccca acgccgcgac tgcggacggc tacggcagta tgatggaggt cgagtacgtc    840
gccgtctact cgtcgtaa                                                  858
```

<210> SEQ ID NO 4
<211> LENGTH: 285
<212> TYPE: PRT
<213> ORGANISM: Thielavia terrestris

<400> SEQUENCE: 4

```
Met Arg Ala Ser Ser Leu Thr Ala Leu Ser Phe Phe Ser Ser Leu Val
1               5                   10                  15

Ala Ala Leu Pro Ala Pro Ala Tyr Pro Gly Tyr Thr Leu Leu Trp Ser
            20                  25                  30

Asp Glu Phe Ala Gly Pro Ala Gly Ser Ser Pro Asp Gln Ser Arg Trp
        35                  40                  45

Asn Ile Ile Thr Asn Val His Thr Asn His Glu Val Glu Thr Tyr Thr
    50                  55                  60

Thr Ser Asn Gln Asn Leu Gln Ile Ser Gly Gly Gly Thr Val Gln Ile
65                  70                  75                  80

Val Pro Arg Lys Ser Pro Ser Gly Gln Trp Thr Ser Ala Arg Ile Glu
                85                  90                  95

Ser Lys Ala Thr Phe Thr Pro Ala Ala Gly Lys Val Thr Met Phe Glu
            100                 105                 110

Ala Ala Ile Arg Phe Gly Thr Asn Pro Ala Ser Gln Lys Gln Gly Ile
        115                 120                 125

Trp Pro Ala Phe Trp Leu Leu Gly Asp Ala Ile His Gly Thr Ala
    130                 135                 140

Trp Pro Leu Cys Gly Glu Leu Asp Ile Met Glu Thr Val Asn Gly Leu
145                 150                 155                 160

Pro Thr Gly His Gly Thr Leu His Cys Gly Ala Thr Thr Ser Gly Gly
                165                 170                 175

Pro Cys Ala Glu Pro Thr Gly Arg Thr Gly Ala Val Ala Leu Pro Asp
            180                 185                 190

Asp Gly Trp His Thr Trp Ser Leu Gln Ile Asp Arg Thr Asn Ala Ala
        195                 200                 205

Gly Gly Trp Ala Gly Glu Val Ile Lys Phe Leu Lys Asp Gly Gln Val
    210                 215                 220

Phe Phe Gln Val Ser Gly Ala Gln Leu Gly Asp Glu Gly Ile Trp Ala
225                 230                 235                 240

Thr Leu Ala His Ser Pro Leu Phe Ile Ile Leu Asn Val Ala Val Gly
                245                 250                 255

Gly Asp Trp Pro Gly Ala Pro Asn Ala Ala Thr Ala Asp Gly Tyr Gly
            260                 265                 270

Ser Met Met Glu Val Glu Tyr Val Ala Val Tyr Ser Ser
        275                 280                 285
```

<210> SEQ ID NO 5
<211> LENGTH: 32
<212> TYPE: DNA
<213> ORGANISM: Thielavia terrestris

<400> SEQUENCE: 5

```
tcgtcgggga caactttgta caaaaaagtt gg                                  32
```

<210> SEQ ID NO 6

```
<211> LENGTH: 27
<212> TYPE: DNA
<213> ORGANISM: Thielavia terrestris

<400> SEQUENCE: 6
cccctgttga aacatgtttt ttcaacc                                              27

<210> SEQ ID NO 7
<211> LENGTH: 16
<212> TYPE: DNA
<213> ORGANISM: Thielavia terrestris

<400> SEQUENCE: 7
gtaaaacgac ggccag                                                          16

<210> SEQ ID NO 8
<211> LENGTH: 25
<212> TYPE: DNA
<213> ORGANISM: Thielavia terrestris
<220> FEATURE:
<221> NAME/KEY: misc_feature
<222> LOCATION: (24)..(24)
<223> OTHER INFORMATION: V = A, C, OR G
<220> FEATURE:
<221> NAME/KEY: misc_feature
<222> LOCATION: (25)..(25)
<223> OTHER INFORMATION: N = A, C, G, OR T

<400> SEQUENCE: 8
tttttttttt tttttttttt tttvn                                                25
```

POLYPEPTIDES HAVING ENDOGLUCANASE ACTIVITY AND POLYNUCLEOTIDES ENCODING SAME

CROSS-REFERENCE TO RELATED APPLICATION

This application is a divisional application of U.S. patent application Ser. No. 13/600,071, filed Aug. 30, 2012, now U.S. Pat. No. 8,465,958, which is a divisional application of U.S. patent application Ser. No. 12/763,578, filed Apr. 20, 2010, now U.S. Pat. No. 8,268,606, which is a divisional application of U.S. patent application Ser. No. 12/327,509, filed Dec. 3, 2008, now U.S. Pat. No. 7,741,074, which claims the benefit of U.S. Provisional Application No. 60/992,576, filed Dec. 5, 2007, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

REFERENCE TO A SEQUENCE LISTING

This application contains a Sequence Listing in computer readable form. The computer readable form is incorporated herein by reference.

REFERENCE TO DEPOSITS OF BIOLOGICAL MATERIAL

This application contains a reference to deposits of biological material, which deposits are incorporated herein by reference.

BACKGROUND OF THE INVENTION

1. Field of the Invention

The present invention relates to isolated polypeptides having endoglucanase activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose can be easily fermented by yeast into ethanol.

Kvesitadaze et al., 1995, *Applied Biochemistry and Biotechnology* 50: 137-143, describe the isolation and properties of a thermostable endoglucanase from a thermophilic mutant strain of *Thielavia terrestris*. Gilbert et al., 1992, *Bioresource Technology* 39: 147-154, describe the characterization of the enzymes present in the cellulase system of *Thielavia terrestris* 255B. Breuil et al., 1986, *Biotechnology Letters* 8: 673-676, describe production and localization of cellulases and beta-glucosidases from *Thielavia terrestris* strains C464 and NRRL 8126.

The present invention relates to polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide comprising an amino acid sequence having at least 60% identity to the mature polypeptide of SEQ ID NO: 2 or SEQ ID NO: 4;

(b) a polypeptide encoded by a polynucleotide that hybridizes under at least medium stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii);

(c) a polypeptide encoded by a polynucleotide comprising a nucleotide sequence having at least 60% identity to the mature polypeptide coding sequence of SEQ ID NO: 1 or SEQ ID NO: 3; and (d) a variant comprising a substitution, deletion, and/or insertion of one or more (several) amino acids of the mature polypeptide of SEQ ID NO: 2 or SEQ ID NO: 4.

The present invention also relates to isolated polynucleotides encoding polypeptides having endoglucanase activity, selected from the group consisting of:

(a) a polynucleotide encoding a polypeptide comprising an amino acid sequence having at least 60% identity to the mature polypeptide of SEQ ID NO: 2 or SEQ ID NO: 4;

(b) a polynucleotide that hybridizes under at least medium stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii);

(c) a polynucleotide comprising a nucleotide sequence having at least 60% identity to the mature polypeptide coding sequence of SEQ ID NO: 1 or SEQ ID NO: 3; and (d) a polynucleotide encoding a variant comprising a substitution, deletion, and/or insertion of one or more (several) amino acids of the mature polypeptide of SEQ ID NO: 2 or SEQ ID NO: 4.

The present invention also relates to nucleic acid constructs, recombinant expression vectors, recombinant host cells comprising the polynucleotides, and methods of producing a polypeptide having endoglucanase activity.

The present invention also relates to methods of inhibiting the expression of a polypeptide having endoglucanase activity in a cell, comprising administering to the cell or expressing in the cell a double-stranded RNA (dsRNA) molecule, wherein the dsRNA comprises a subsequence of a polynucleotide of the present invention. The present also relates to a double-stranded inhibitory RNA (dsRNA) molecule, wherein optionally the dsRNA is a siRNA or a miRNA molecule.

The present invention also relates to methods of using the polypeptides having endoglucanase activity in the degradation or conversion of cellulosic material.

The present invention also relates to plants comprising an isolated polynucleotide encoding a polypeptide having endoglucanase activity.

The present invention also relates to methods of producing a polypeptide having endoglucanase, comprising: (a) cultivating a transgenic plant or a plant cell comprising a polynucleotide encoding the polypeptide having endoglucanase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 20 of SEQ ID NO: 2 or amino acids 1 to 18 of SEQ ID NO: 4, wherein the gene is foreign to the nucleotide sequence.

BRIEF DESCRIPTION OF THE FIGURES

FIGS. 1A and 1B show the cDNA sequence and the deduced amino acid sequence of a *Thielavia terrestris* NRRL 8126 CEL16A endoglucanase (SEQ ID NOs: 1 and 2, respectively).

FIG. 2 shows the cDNA sequence and the deduced amino acid sequence of a *Thielavia terrestris* NRRL 8126 CEL16B endoglucanase (SEQ ID NOs: 3 and 4, respectively).

DEFINITIONS

Figure 3:
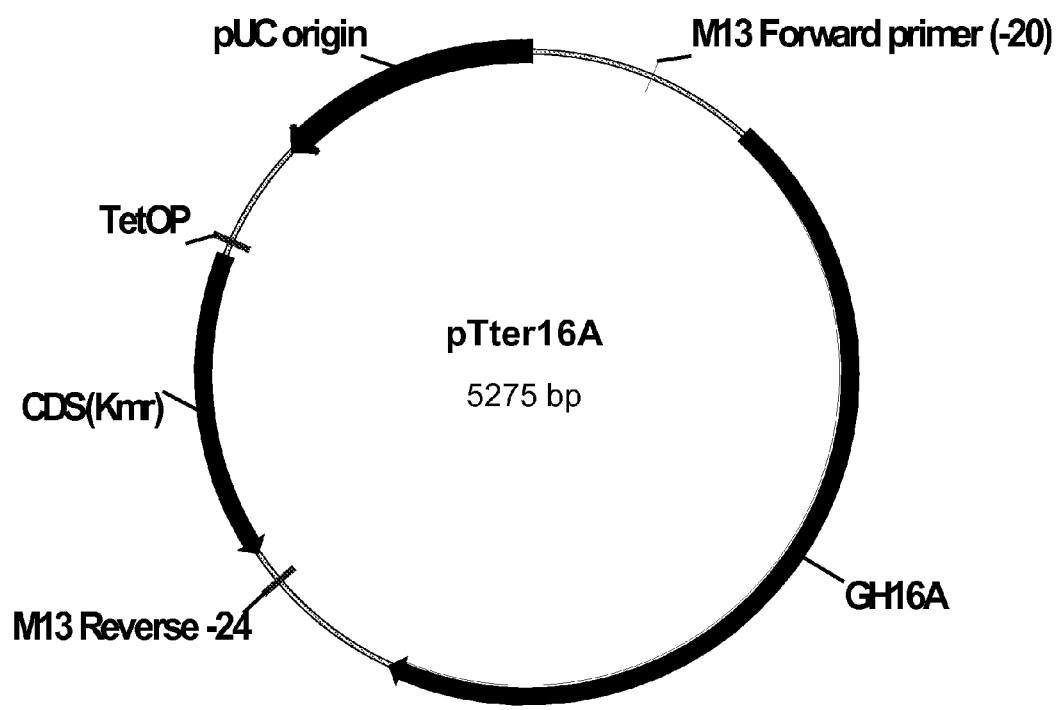
FIG. 3 shows a restriction map of pTter16A.

Endoglucanase activity: The term "endoglucanase activity" is defined herein as an endo-1,4-beta-D-glucan 4-glucanohydrolase activity (E.C. No. 3.2.1.4) that catalyses the endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 µmole of reducing sugars produced per minute at 50° C., pH 4.8.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of the mature polypeptide of SEQ ID NO: 2 or SEQ ID NO: 4.

Family 16 or Family GH16 or CEL16: The term "Family 16" or "Family GH16" or "CEL16" is defined herein as a polypeptide falling into the glycoside hydrolase Family 16 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Cellulolytic activity: The term "cellulolytic activity" is defined herein as a biological activity that hydrolyzes a cellulosic material. Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate. For CELLUCLAST™ (*Trichoderma reesei* cellulase; Novozymes A/S, Bagsværd, Denmark) the assay is carried out at 40° C. in 0.1 M phosphate pH 9.0 buffer for 30 minutes with CMC as substrate (33.3 g/L carboxymethyl cellulose Hercules 7 LFD) and an enzyme concentration of approximately 3.3-4.2 CEVU/ml. The CEVU activity is calculated relative to a declared enzyme standard, such as CELLUZYME™ Standard 17-1194 (obtained from Novozymes A/S, Bagsværd, Denmark).

For purposes of the present invention, cellulolytic activity can be determined by measuring the increase in hydrolysis of a cellulosic material by a cellulolytic mixture under the following conditions: 1-10 mg of cellulolytic protein/g of cellulose in PCS for 5-7 day at 50° C. compared to a control hydrolysis without addition of cellulolytic protein.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method can be employed to assess hydrolysis of cellulose in corn stover, while the method of van Tilbeurgh et al. can be used to determine cellobiohydrolase activity on a fluorescent disaccharide derivative.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% TWEEN® 20.

Cellulosic material: The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

The cellulosic material can be any material containing cellulose. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue The cellulosic material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another preferred aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

The cellulosic material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Pretreated corn stover: The term "PCS" or "Pretreated Corn Stover" is defined herein as a cellulosic material derived from corn stover by treatment with heat and dilute acid.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide in its final form following translation and any post-translational modifications, such as N-terminal processing, C-terminal truncation, glycosylation, phosphorylation, etc. In a preferred aspect, the mature polypeptide is amino acids 21 to 797 of SEQ ID NO: 2 based on the SignalP software program (Nielsen et al., 1997, *Protein Engineering* 10: 1-6) that predicts amino acids 1 to 20 of SEQ ID NO: 2 are a signal peptide. In another preferred aspect, the mature polypeptide is amino acids 19 to 285 of SEQ ID NO: 4 based on the SignalP software program that predicts amino acids 1 to 18 of SEQ ID NO: 4 are a signal peptide.

Mature polypeptide coding sequence: The term "mature polypeptide coding sequence" is defined herein as a nucleotide sequence that encodes a mature polypeptide having endoglucanase activity. In a preferred aspect, the mature polypeptide coding sequence is nucleotides 61 to 1428 of SEQ ID NO: 1 based on the SignalP software program that predicts nucleotides 1 to 60 encode a signal peptide. In another preferred aspect, the mature polypeptide coding sequence is nucleotides 55 to 855 of SEQ ID NO: 3 based on the SignalP software program that predicts nucleotides 1 to 54 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLO-SUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that has an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Thielavia terrestris* endoglucanase of SEQ ID NO: 2 or SEQ ID NO: 4, or the mature polypeptides thereof.

Polypeptide fragment: The term "polypeptide fragment" is defined herein as a polypeptide having one or more (several) amino acids deleted from the amino and/or carboxyl terminus of the mature polypeptide of SEQ ID NO: 2 or SEQ ID NO: 4; or a homologous sequence thereof; wherein the fragment has endoglucanase activity. In a preferred aspect, a fragment contains at least 660 amino acid residues, more preferably at least 700 amino acid residues, and most preferably at least 740 amino acid residues, of the mature polypeptide of SEQ ID NO: 2 or a homologous sequence thereof. In another preferred aspect, a fragment contains at least 225 amino acid residues, more preferably at least 240 amino acid residues, and most preferably at least 255 amino acid residues, of the mature polypeptide of SEQ ID NO: 4 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having endoglucanase activity. In a preferred aspect, a subsequence contains at least 1980 nucleotides, more preferably at least 2100 nucleotides, and most preferably at least 2220 nucleotides of the mature polypeptide coding sequence of SEQ ID NO: 1 or a homologous sequence thereof. In another preferred aspect, a subsequence contains at least 675 nucleotides, more preferably at least 720 nucleotides, and most preferably at least 765 nucleotides of the mature polypeptide coding sequence of SEQ ID NO: 3 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may bey present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term nucleic acid construct is synonymous with the term "expression cassette" when the nucleic acid construct contains the control sequences required for expression of a coding sequence of the present invention.

Control sequences: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2 or SEQ ID NO: 4; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having endoglucanase activity produced by an organism expressing a modified polynucleotide sequence of the mature polypeptide coding sequence of SEQ ID NO: 1 or SEQ ID NO: 3; or a homologous sequence thereof. The modified nucleotide sequence is obtained through human intervention by modification of the polynucleotide sequence disclosed in SEQ ID NO: 1 or SEQ ID NO: 3; or a homologous sequence thereof.

DETAILED DESCRIPTION OF THE INVENTION

Polypeptides Having Endoglucanase Activity

In a first aspect, the present invention relates to isolated polypeptides comprising an amino acid sequence having a degree of identity to the mature polypeptide of SEQ ID NO: 2 or SEQ ID NO: 4 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have endoglucanase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2 or SEQ ID NO: 4.

A polypeptide of the present invention preferably comprises the amino acid sequence of SEQ ID NO: 2 or an allelic variant thereof; or a fragment thereof having endoglucanase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 21 to 797 of SEQ ID NO: 2, or an allelic variant thereof; or a fragment thereof having endoglucanase activity. In another preferred aspect, the polypeptide comprises amino acids 21 to 797 of SEQ ID NO: 2. In another preferred aspect, the polypeptide consists of the amino acid sequence of SEQ ID NO: 2 or an allelic variant thereof; or a fragment thereof having endoglucanase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 21 to 797 of SEQ ID NO: 2 or an allelic variant thereof; or a fragment thereof having endoglucanase activity. In another preferred aspect, the polypeptide consists of amino acids 21 to 797 of SEQ ID NO: 2.

A polypeptide of the present invention also preferably comprises the amino acid sequence of SEQ ID NO: 4 or an allelic variant thereof; or a fragment thereof having endoglucanase activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 19 to 285 of SEQ ID NO: 4, or an allelic variant thereof; or a fragment thereof having endoglucanase activity. In another preferred aspect, the polypeptide comprises amino acids 19 to 285 of SEQ ID NO: 4. In another preferred aspect, the polypeptide consists of the amino acid sequence of SEQ ID NO: 4 or an allelic variant thereof; or a fragment thereof having endoglucanase activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 19 to 285 of SEQ ID NO: 4 or an allelic variant thereof; or a fragment thereof having endoglucanase activity. In another preferred aspect, the polypeptide consists of amino acids 19 to 285 of SEQ ID NO: 4.

In a second aspect, the present invention relates to isolated polypeptides having endoglucanase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 or SEQ ID NO: 3 contains at least 100 contiguous nucleotides or preferably at least 200 contiguous nucleotides. Moreover, the subsequence may encode a polypeptide fragment having endoglucanase activity. In a preferred aspect, the complementary strand is the full-length complementary strand of the mature polypeptide coding sequence of SEQ ID NO: 1 or SEQ ID NO: 3.

The nucleotide sequence of SEQ ID NO: 1 or SEQ ID NO: 3; or a subsequence thereof; as well as the amino acid sequence of SEQ ID NO: 2 or SEQ ID NO: 4; or a fragment thereof; may be used to design nucleic acid probes to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, or most preferably at least 800 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1 or SEQ ID NO: 3; the genomic DNA sequence comprising the mature polypeptide coding sequence of SEQ ID NO: 1 or SEQ ID NO: 3; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 61 to 1428 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pTter16A which is contained in *E. coli* NRRL B-50081, wherein the polynucleotide sequence thereof encodes a polypeptide having endoglucanase activity. In another preferred aspect, the nucleic acid probe is the mature polypeptide coding region contained in plasmid pTter16A which is contained in *E. coli* NRRL B-50081.

In another preferred aspect, the nucleic acid probe is the mature polypeptide coding sequence of SEQ ID NO: 3. In another preferred aspect, the nucleic acid probe is nucleotides 55 to 855 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pTter16B which is contained in *E. coli* NRRL B-50082, wherein the polynucleotide sequence thereof encodes a polypeptide having endoglucanase activity. In another preferred aspect, the nucleic acid probe is the mature polypeptide coding region contained in plasmid pTter16B which is contained in *E. coli* NRRL B-50082.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having endoglucanase activity encoded by polynucleotides comprising or consisting of nucleotide sequences that have a degree of identity to the mature polypeptide coding sequence of SEQ ID NO: 1 or SEQ ID NO: 3 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having endoglucanase activity. See polynucleotide section herein.

In a fourth aspect, the present invention relates to artificial variants comprising a substitution, deletion, and/or insertion of one or more (or several) amino acids of the mature polypeptide of SEQ ID NO: 2 or SEQ ID NO: 4; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 or SEQ ID NO: 4 is 10, preferably 9, more preferably 8, more preferably 7, more preferably at most 6, more preferably 5, more preferably 4, even more preferably 3, most preferably 2, and even most preferably 1.

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having endoglucanase activity of the present invention may be a bacterial polypeptide. For example, the polypeptide may be a gram positive bacterial polypeptide such as a Bacillus, Streptococcus, Streptomyces, Staphylococcus, Enterococcus, Lactobacillus, Lactococcus, Clostridium, Geobacillus, or Oceanobacillus polypeptide having endoglucanase activity, or a Gram negative bacterial polypeptide such as an E. coli, Pseudomonas, Salmonella, Campylobacter, Helicobacter, Flavobacterium, Fusobacterium, Ilyobacter, Neisseria, or Ureaplasma polypeptide having endoglucanase activity.

In a preferred aspect, the polypeptide is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis polypeptide having endoglucanase activity.

In another preferred aspect, the polypeptide is a Streptococcus equisimilis, Streptococcus pyogenes, Streptococcus uberis, or Streptococcus equi subsp. Zooepidemicus polypeptide having endoglucanase activity.

In another preferred aspect, the polypeptide is a Streptomyces achromogenes, Streptomyces avermitilis, Streptomyces coelicolor, Streptomyces griseus, or Streptomyces lividans polypeptide having endoglucanase activity.

A polypeptide having endoglucanase activity of the present invention may also be a fungal polypeptide, and more preferably a yeast polypeptide such as a Candida, Kluyveromyces, Pichia, Saccharomyces, Schizosaccharomyces, or Yarrowia polypeptide having endoglucanase activity; or more preferably a filamentous fungal polypeptide such as an Acremonium, Agaricus, Alternaria, Aspergillus, Aureobasidium,

*Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having endoglucanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having endoglucanase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Trichoderma harzianum, Trichoderma koningii, Trichoderma longibrachiatum, Trichoderma reesei,* or *Trichoderma viride* polypeptide having endoglucanase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila,* or *Thielavia terrestris* polypeptide.

In a more preferred aspect, the polypeptide is a *Thielavia terrestris* polypeptide having endoglucanase activity. In a most preferred aspect, the polypeptide is a *Thielavia terrestris* NRRL 8126 polypeptide having endoglucanase activity, e.g., the polypeptide comprising the mature polypeptide of SEQ ID NO: 2 or SEQ ID NO: 4.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having endoglucanase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Bio/technology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having endoglucanase activity of the present invention.

In a preferred aspect, the nucleotide sequence comprises or consists of SEQ ID NO: 1. In another more preferred aspect, the nucleotide sequence comprises or consists of the sequence contained in plasmid pTter16A which is contained in *E. coli* NRRL B-50081. In another preferred aspect, the nucleotide sequence comprises or consists of the mature polypeptide coding sequence of SEQ ID NO: 1. In another preferred aspect, the nucleotide sequence comprises or consists of nucleotides 61 to 1428 of SEQ ID NO: 1. In another more preferred aspect, the nucleotide sequence comprises or consists of the mature polypeptide coding sequence contained in plasmid pTter16A which is contained in *E. coli* NRRL B-50081. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have endoglucanase activity.

In another preferred aspect, the nucleotide sequence comprises or consists of SEQ ID NO: 3. In another more preferred aspect, the nucleotide sequence comprises or consists of the sequence contained in plasmid pTter16B which is contained in E. coli NRRL B-50082. In another preferred aspect, the nucleotide sequence comprises or consists of the mature polypeptide coding sequence of SEQ ID NO: 3. In another preferred aspect, the nucleotide sequence comprises or consists of nucleotides 55 to 855 of SEQ ID NO: 3. In another more preferred aspect, the nucleotide sequence comprises or consists of the mature polypeptide coding sequence contained in plasmid pTter16B which is contained in E. coli NRRL B-50082. The present invention also encompasses nucleotide sequences that encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 that encode fragments of SEQ ID NO: 4 that have endoglucanase activity.

The present invention also relates to mutant polynucleotides comprising or consisting of at least one mutation in the mature polypeptide coding sequence of SEQ ID NO: 1 or SEQ ID NO: 3, in which the mutant nucleotide sequence encodes the mature polypeptide of SEQ ID NO: 2 or SEQ ID NO: 4, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 or SEQ ID NO: 3 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1 or SEQ ID NO: 3, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1 or SEQ ID NO: 3.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii); and (b) isolating the hybridizing polynucleotide, which encodes a polypeptide having endoglucanase activity. In a preferred aspect, the complementary strand is the full-length complementary strand of the mature polypeptide coding sequence of SEQ ID NO: 1 or SEQ ID NO: 3.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* endoglucanase I, *Trichoderma reesei* endoglucanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 20 of SEQ ID NO: 2. In another preferred aspect, the signal peptide coding sequence comprises or consists of nucleotides 1 to 60 of SEQ ID NO: 1.

In another preferred aspect, the signal peptide comprises or consists of amino acids 1 to 18 of SEQ ID NO: 4. In another preferred aspect, the signal peptide coding sequence comprises or consists of nucleotides 1 to 54 of SEQ ID NO: 3.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids*

Res. 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota*, and *Zygomycota* (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1 or SEQ ID NO: 3, wherein the mutant nucleotide sequence encodes a polypeptide that comprises or consists of the mature polypeptide of SEQ ID NO: 2 or SEQ ID NO: 4, respectively; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having endoglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having endoglucanase activity of the present invention under conditions conducive for production of the polypeptide; and (b) recovering the polypeptide.

Removal or Reduction of Endoglucanase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of endoglucanase activity by fermentation of a cell that produces both a polypeptide of the present invention as well as the protein product of interest by adding an effective amount of an agent capable of inhibiting endoglucanase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of endoglucanase activity by cultivating the cell under conditions permitting the expression of the product, subjecting the resultant culture broth to a combined pH and temperature treatment so as to reduce the endoglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an endoglucanase inhibitor.

In accordance with this aspect of the invention, it is possible to remove at least 60%, preferably at least 75%, more preferably at least 85%, still more preferably at least 95%, and most preferably at least 99% of the endoglucanase activity. Complete removal of endoglucanase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially endoglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or endoglucanase. The endoglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity that is produced by a method of the present invention.

Methods of Inhibiting Expression of a Polypeptide Having Endoglucanase Activity

The present invention also relates to methods of inhibiting the expression of a polypeptide having endoglucanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 or SEQ ID NO: 3 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNA is of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or endoglucanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention also relates to methods for degrading or converting a cellulosic material, comprising: treating the cellulosic material with a composition comprising one or more cellulolytic proteins in the presence of a polypeptide having endoglucanase activity of the present invention. In a preferred aspect, the method further comprises recovering the degraded or converted cellulosic material.

The present invention further relates to methods of producing a fermentation product, comprising: (a) saccharifying a cellulosic material with a composition comprising one or more cellulolytic proteins in the presence of a polypeptide having endoglucanase activity of the present invention; (b) fermenting the saccharified cellulosic material of step (a) with one or more fermenting microorganisms to produce the fermentation product; and (c) recovering the fermentation product from the fermentation.

The composition comprising the polypeptide having endoglucanase activity can be in the form of a crude fermentation broth with or without the cells removed or in the form of a semi-purified or purified enzyme preparation or the composition can comprise a host cell of the present invention as a source of the polypeptide having endoglucanase activity in a fermentation process with the biomass.

The methods of the present invention can be used to saccharify a cellulosic material to fermentable sugars and convert the fermentable sugars to many useful substances, e.g., chemicals and fuels. The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); SHCF (separate hydrolysis and co-fermentation), HHCF (hybrid hydrolysis and fermentation), and direct microbial conversion (DMC). SHF uses separate process steps to first enzymatically hydrolyze lignocellulose to fermentable sugars, e.g., glucose, cellobiose, cellotriose, and pentose sugars, and then ferment the fermentable sugars to ethanol. In SSF, the enzymatic hydrolysis of lignocellulose and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis separate step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, lignocellulose hydrolysis, and fermentation) in one or more steps where the same organism is used to produce the enzymes for conversion of the lignocellulose to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: Fluidized bed, upflow blanket, immobilized, and extruder type reactors for hydrolysis and/or fermentation.

Pretreatment.

In practicing the methods of the present invention, any pretreatment process known in the art can be used to disrupt the plant cell wall components. The cellulosic material can also be subjected to pre-soaking, wetting, or conditioning prior to pretreatment using methods known in the art. Conventional pretreatments include, but are not limited to, steam pretreatment (with or without explosion), dilute acid pretreatment, hot water pretreatment, lime pretreatment, wet oxidation, wet explosion, ammonia fiber explosion, organosolv pretreatment, and biological pretreatment. Additional pretreatments include ultrasound, electroporation, microwave, supercritical $CO_2$, supercritical $H_2O$, and ammonia percolation pretreatments.

The cellulosic material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulosic material with one or more cellulolytic enzymes, or other enzyme activities, to release fermentable sugars, such as glucose and/or maltose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulase, accessible to enzymes. The lignocellulose material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121:1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121:

219-230). Sulphuric acid is usually added as a catalyst. In organosolv pretreatment, the majority of the hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof to promote the separation and/or release of cellulose, hemicellulose and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the pretreated cellulosic material is hydrolyzed to break down cellulose and alternatively also hemicellulose to fermentable sugars, such as glucose, xylose, xylulose, arabinose, maltose, mannose, galactose, or soluble oligosaccharides. The hydrolysis is performed enzymatically by a cellulolytic enzyme composition comprising an effective amount of a polypeptide having endoglucanase activity of the present invention, which can further comprise one or more hemicellulolytic enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

In addition to a polypeptide having endoglucanase activity of the present invention, the cellulolytic enzyme components of the composition are preferably enzymes having endoglucanase, cellobiohydrolase, and beta-glucosidase activities. In a preferred aspect, the cellulolytic enzyme composition further comprises one or more polypeptides having cellulolytic enhancing activity (see, for example, WO 2005/074647, WO 2005/074656, and U.S. Published Application Serial No. 2007/0077630, which are incorporated herein by reference). In another preferred aspect, the cellulolytic enzyme preparation is supplemented with one or more additional enzyme activities selected from the group consisting of hemicellulases, esterases (e.g., lipases, phospholipases, and/or cutinases), proteases, laccases, peroxidases, or mixtures thereof. In the methods of the present invention, the additional enzyme(s) can be added prior to or during fermentation, including during or after propagation of the fermenting microorganism(s).

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes used in the present invention can be in any form suitable for use in the methods described herein, such as a crude fermentation broth with or without cells or substantially pure polypeptides. The enzyme(s) can be a dry powder or granulate, a non-dusting granulate, a liquid, a stabilized liquid, or a protected enzyme(s). Granulates can be produced, e.g., as disclosed in U.S. Pat. Nos. 4,106,991 and 4,661,452, and can optionally be coated by process known in the art. Liquid enzyme preparations can, for instance, be stabilized by adding stabilizers such as a sugar, a sugar alcohol or another polyol, and/or lactic acid or another organic acid according to established process. Protected enzymes can be prepared according to the process disclosed in EP 238,216.

The optimum amounts of the enzymes and polypeptides having cellulolytic enhancing activity depend on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic protein(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of a polypeptide having endoglucanase activity to cellulosic material is about 0.01 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of polypeptide(s) having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation.

The fermentable sugars obtained from the pretreated and hydrolyzed cellulosic material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF); simultaneous saccharification and fermentation (SSF); simultaneous saccharification and cofermentation (SSCF); hybrid hydrolysis and fermentation (HHF); SHCF (separate hydrolysis and co-fermentation), HHCF (hybrid hydrolysis and fermentation), and direct microbial conversion (DMC).

Any suitable hydrolyzed cellulosic material can be used in the fermentation step in practicing the present invention. The material is generally selected based on the desired fermentation product, i.e., the substance to be obtained from the fermentation, and the process employed, as is well known in the art. Examples of substrates suitable for use in the methods of present invention, include cellulose-containing materials, such as wood or plant residues or low molecular sugars DP1-3 obtained from processed cellulosic material that can be metabolized by the fermenting microorganism, and which can be supplied by direct addition to the fermentation medium.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of the *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Klyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another more preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded lignocellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth.

Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to nucleic acid constructs comprising a gene encoding a protein, wherein the gene is operably linked to a nucleotide sequence encoding a signal peptide comprising or consisting of amino acids 1 to 20 of SEQ ID NO: 2 or amino acids 1 to 18 of SEQ ID NO: 4, wherein the gene is foreign to the nucleotide sequence.

In a preferred aspect, the nucleotide sequence comprises or consists of nucleotides 1 to 60 of SEQ ID NO: 1. In another preferred aspect, the nucleotide sequence comprises or consists of nucleotides 1 to 54 of SEQ ID NO: 3.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or endoglucanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strain

*Thielavia terrestris* NRRL 8126 was used as the source of genes encoding Family 16 polypeptides having endoglucanase activity.

Media

PDA plates were composed per liter of 39 grams of potato dextrose agar.

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, 1 ml of COVE trace metals solution, and sufficient $K_2HPO_4$ to achieve a final pH of 5.4.

NNCYPmod medium was composed per liter of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, 1 ml of COVE trace metals solution, and sufficient $K_2HPO_4$ to achieve a final pH of approximately 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

LB plates were composed per liter of 10 g of tryptone, 5 g of yeast extract, 5 g of sodium chloride, and 15 g of Bacto Agar.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 µl of AMG trace metals solution; the pH was adjusted to 5.0 and then filter sterilized with a 0.22 µm filtering unit.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

Freezing medium was composed of 60% SOC medium and 40% glycerol.

2×YT medium was composed per liter of 16 g of tryptone, 10 g of yeast extract, 5 g of NaCl, and 15 g of Bacto agar.

Example 1

Expressed Sequence Tags (EST) cDNA Library Construction

*Thielavia terrestris* NRRL 8126 was cultivated in 50 ml of NNCYPmod medium supplemented with 1% glucose in a 250 ml flask at 45° C. for 24 hours with shaking at 200 rpm. A two ml aliquot from the 24-hour liquid culture of *Thielavia terrestris* NRRL 8126 was used to seed a 500 ml flask containing 100 ml of NNCYPmod medium supplemented with 2% SIGMACELL® 20 (Sigma Chemical Co., St. Louis, Mo., USA). The culture was incubated at 45° C. for 3 days with shaking at 200 rpm. The mycelia were harvested by filtration through a funnel with a glass fiber prefilter (Nalgene, Rochester, N.Y., USA), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of FENAZOL™ (Ambion, Inc., Austin, Tex., USA) in a 50 ml FALCON® tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

The quality and quantity of the purified RNA was assessed with an AGILENT® 2100 Bioanalyzer (Agilent Technologies, Inc., Palo Alto, Calif., USA). Polyadenylated mRNA was isolated from 360 µg of total RNA with the aid of a POLY(A)PURIST™ Magnetic Kit (Ambion, Inc., Austin, Tex., USA) according to the manufacturer's instructions.

To create the cDNA library, a CLONEMINER™ Kit (Invitrogen Corp., Carlsbad, Calif., USA) was employed to construct a directional library that does not require the use of restriction enzyme cloning, thereby reducing the number of chimeric clones and size bias.

To insure the successful synthesis of the cDNA, two reactions were performed in parallel with two different concentrations of mRNA (2.2 and 4.4 µg of poly (A)$^+$ mRNA). The mRNA samples were mixed with a Biotin-attB2-Oligo(dt) primer (Invitrogen Corp., Carlsbad, Calif., USA), 1× first strand buffer (Invitrogen Corp., Carlsbad, Calif., USA), 2 µl of 0.1 M dithiothreitol (DTT), 10 mM of each dNTP, and water to a final volume of 18 and 16 µl, respectively.

The reaction mixtures were mixed and then 2 and 4 µl of SUPERSCRIPT™ reverse transcriptase (Invitrogen Corp., Carlsbad, Calif., USA) were added. The reaction mixtures were incubated at 45° C. for 60 minutes to synthesize the first complementary strand. For second strand synthesis, to each first strand reaction was added 30 µl of 5× second strand buffer (Invitrogen Corp., Carlsbad, Calif., USA), 3 µl of 10 mM of each dNTP, 10 units of *E. coli* DNA ligase (Invitrogen Corp., Carlsbad, Calif., USA), 40 units of *E. coli* DNA polymerase I (Invitrogen Corp., Carlsbad, Calif., USA), and 2 units of *E. coli* RNase H (Invitrogen Corp., Carlsbad, Calif., USA) in a total volume of 150 µl. The mixtures were then incubated at 16° C. for two hours. After the two-hour incubation 2 µl of T4 DNA polymerase (Invitrogen Corp., Carlsbad, Calif., USA) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 µg of glycogen, 120 µl of 5 M ammonium acetate, and 660 µl of ethanol. After centrifugation at 12,000×g for 30 minutes at 4° C., the cDNA pellets were washed with cold 70% ethanol, dried under vacuum for 2-3 minutes, and resuspended in 18 µl of DEPC-water. To each resuspended cDNA sample were added 10 µl of 5× adapted buffer (Invitrogen Corp., Carlsbad, Calif., USA), 10 µg of each attB1 adapter (Invitrogen Corp., Carlsbad, Calif., USA), 7 µl of 0.1 M DTT, and 5 units of T4 DNA ligase (Invitrogen Corp., Carlsbad, Calif., USA).

Ligation reactions were incubated overnight at 16° C. Excess adapters were removed by size-exclusion chromatography in 1 ml of SEPHACRYL™ S-500 HR resin (Amersham Biosciences, Piscataway, N.J., USA). Column fractions were collected according to the CLONEMINER™ Kit's instructions and fractions 3 to 14 were analyzed with an AGILENT® 2100 Bioanalyzer to determine the fraction at which the attB1 adapters started to elute. This analysis showed that the adapters began eluting around fraction 10 or 11. For the first library fractions 6-11 were pooled and for the second library fractions 4-11 were pooled.

Cloning of the cDNA was performed by homologous DNA recombination according to the GATEWAY® System protocol (Invitrogen Corp., Carlsbad, Calif., USA) using BP CLONASE™ (Invitrogen Corp., Carlsbad, Calif., USA) as the recombinase. Each BP CLONASE™ recombination reaction contained approximately 70 ng of attB-flanked-cDNA, 250 ng of pDONR™ 222, 2 µl of 5×BP CLONASE™ buffer, 2 µl of TE, and 3 µl of BP CLONASE™. All reagents were obtained from Invitrogen, Carlsbad, Calif., USA. Recombination reactions were incubated at 25° C. overnight.

Heat-inactivated BP recombination reactions were then divided into 6 aliquots and electroporated into ELECTROMAX™ *E. coli* DH10B electrocompetent cells (Invitrogen Corp., Carlsbad, Calif., USA) using a GENE PULSER™ (Bio-Rad Laboratories, Inc., Hercules, Calif., USA) with the following parameters: Voltage: 2.0 kV; Resistance: 200Ω; and Capacity: 25 µF. Electrophorated cells were resuspended in 1 ml of SOC medium and incubated at 37° C. for 60 minutes with constant shaking at 200 rpm. After the incubation period, the transformed cells were pooled and mixed 1:1 with freezing medium. A 200 µl aliquot was removed for library titration and then the rest of each library was aliquoted into 1.8 ml cryovials (Wheaton Science Products, Millville, N.J., USA) and stored frozen at −80° C.

Four serial dilutions of each library were prepared: 1/100, 1/1000, 1/10$^4$, and 1/10$^5$. From each dilution 100 µl were plated onto 150 mm LB plates supplemented with 50 µg of kanamycin per ml and incubated at 37° C. overnight. The number of colonies on each dilution plate was counted and used to calculate the total number of transformants in each library.

The first library contained approximately 5.4 million independent clones and the second library contained approximately 9 million independent clones.

Example 2

Template Preparation and Nucleotide Sequencing of cDNA Clones

Aliquots from both libraries described in Example 1 were mixed and plated onto 25×25 cm LB plates supplemented with 50 µg of kanamycin per ml. Individual colonies were arrayed onto 96-well plates containing 100 µl of LB medium supplemented with 50 µg of kanamycin per ml with the aid of a QPix Robot (Genetix Inc., Boston, Mass., USA). Forty-five 96-well plates were obtained for a total of 4320 individual clones. The plates were incubated overnight at 37° C. with shaking at 200 rpm. After incubation, 100 µl of sterile 50% glycerol was added to each well. The transformants were replicated with the aid of a 96-pin tool (Boekel, Feasterville, Pa., USA) into secondary, deep-dish 96-well microculture plates (Advanced Genetic Technologies Corporation, Gaithersburg, Md., USA) containing 1 ml of MAGNIFICENT BROTH™ (MacConnell Research, San Diego, Calif., USA) supplemented with 50 µg of kanamycin per ml in each well. The primary microtiter plates were stored frozen at −80° C. The secondary deep-dish plates were incubated at 37° C. overnight with vigorous agitation at 300 rpm on a rotary shaker. To prevent spilling and cross-contamination, and to allow sufficient aeration, each secondary culture plate was covered with a polypropylene pad (Advanced Genetic Technologies Corporation, Gaithersburg, Md., USA) and a plastic microtiter dish cover. Plasmid DNA was prepared with a Robot-Smart 384 (MWG Biotech Inc., High Point, N.C., USA) and a MONTAGE™ Plasmid Miniprep Kit (Millipore, Billerica, Mass., USA).

Sequencing reactions were performed using BIGDYE® (Applied Biosystems, Inc., Foster City, Calif., USA) terminator chemistry (Giesecke et al., 1992, *Journal of Virology Methods* 38: 47-60) and a M13 Forward (−20) sequencing primer: 5'-GTAAAACGACGGCCAG-3' (SEQ ID NO: 7)

The sequencing reactions were performed in a 384-well format with a Robot-Smart 384. Terminator removal was performed with a MULTISCREEN® Seq384 Sequencing Clean-up Kit (Millipore, Billerica, Mass., USA). Reactions contained 6 µl of plasmid DNA and 4 µl of sequencing mastermix (Applied Biosystems, Foster City, Calif., USA) containing 1 µl of 5× sequencing buffer (Millipore, Billerica, Mass., USA), 1 µl of BIGDYE® terminator (Applied Biosystems, Inc., Foster City, Calif., USA), 1.6 pmoles of M13 Forward primer, and 1 µl of water. Single-pass DNA sequencing was performed with an ABI PRISM Automated DNA Sequencer Model 3700 (Applied Biosystems, Foster City, Calif., USA).

Example 3

Analysis of DNA Sequence Data of cDNA Clones

Base calling, quality value assignment, and vector trimming were performed with the assistance of PHRED/PHRAP software (University of Washington, Seattle, Wash., USA). Clustering analysis of the ESTs was performed with a Transcript Assembler v. 2.6.2. (Paracel, Inc., Pasadena, Calif., USA). Analysis of the EST clustering indicated the presence of 395 independent clusters.

Sequence homology analysis of the assembled EST sequences against the PIR and other databases was performed with the Blastx program (Altschul et. al., 1990, *J. Mol. Biol.* 215:403-410) on a 32-node Linux cluster (Paracel, Inc., Pasadena, Calif., USA) using the BLOSUM 62 matrix (Henikoff, 1992, *Proc. Natl. Acad. Sci. USA* 89: 10915-10919) From these, 246 had hits to known genes in various protein databases and 149 had no significant hits against these databases. Among these 246 genes, 13 had hits against well characterized homologues of glycosyl hydrolase genes.

Example 4

Identification of cDNA Clones Encoding *Thielavia terrestris* Family 16A and 16B Endoglucanases A cDNA clone encoding a *Thielavia terrestris* Family 16A endoglucanase was initially identified by sequence homology to a putative glycosyl hydrolase Family 16 from *Schizosaccharolyces pombe* (GENBANK® accession number NP_595680).

After this initial identification, a clone designated Tter30G12 was retrieved from the original frozen stock plate and streaked onto a LB plate supplemented with 50 µg of kanamycin per ml. The plate was incubated overnight at 37° C. and a single colony from the plate was used to inoculate 3 ml of LB medium supplemented with 150 µg of kanamycin per ml. The liquid culture was incubated overnight at 37° C. and plasmid DNA was prepared with a BIOROBOT® 9600 (QIAGEN Inc., Valencia, Calif., USA). Clone Tter30G12 plasmid DNA was sequenced again with BIGDYE® terminator chemistry as described above, using the M13 forward primer, the M13 reverse primer, and a Poly-T primer shown below to sequence the 3' end of the clone. 5'-TTTTTTTTTTTTTTTTTTTTTTTVN-3' (SEQ ID NO: 8), where V=G, A, C and N=G, A, C, T.

Analysis of the deduced amino acid sequence of clone 30G12 with the Interproscan program (Zdobnov and Apweiler, 2001, *Bioinformatics* 17: 847-8) showed that the amino acid sequence contained the sequence signature of the concanavalin A-like glucanase. This sequence signature known as the InterPro:IPR008985 was found 88 amino acids from the starting amino acid methionine. This region also contained the signature sequence for the active site of the glycosyl hydrolase Family 16, InterPro:IPR008263 confirming that clone Tter30G12 encoded a Family 16 endoglucanase.

The cDNA sequence (SEQ ID NO: 1) and deduced amino acid sequence (SEQ ID NO: 2) are shown in FIGS. 1A and 1B. The cDNA clone encodes a polypeptide of 797 amino acids. The % G+C content of the full-length coding region is 64.5% and of the mature protein coding region (nucleotides 61 to 1428 of SEQ ID NO: 1) is 65%. Using the SignalP software program (Nielsen et al., 1997, *Protein Engineering* 10: 1-6), a signal peptide of 20 residues was predicted. The predicted mature protein contains 777 amino acids with a molecular mass of 80.7 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Thielavia terrestris* endoglucanase gene shared 34% identity (excluding gaps) to the deduced amino acid sequence of identity to *Phaffia rhodozyma* beta-glucanase Family 16 sequence (GENESEQ-P:AAW77311; WO 98/36056).

A cDNA clone encoding a *Thielavia terrestris* Family 16B endoglucanase was initially identified by sequence homology to a glycosyl hydrolase Family 16 from *Rhodothermus marinus* (UNIPROT® accession number P45798).

After this initial identification, a clone designated Tter07B12 was retrieved from the original frozen stock plate and streaked onto a LB plate supplemented with 50 µg of kanamycin per ml. Plasmid DNA was prepared from a culture of this *E. coli* strain and sequenced to completion using the same procedure described above.

Analysis of the deduced amino acid sequence of clone 07B12 with the Interproscan program (Zdobnov and Apweiler, 2001, supra) showed that the amino acid sequence contained the sequence signature of the concanavalin A-like glucanase. This sequence signature known as the InterPro: IPR008985 was found 58 amino acids from the starting amino acid methionine. This region also contained the signature sequence for the active site of the glycosyl hydrolase Family 16, InterPro:IPR008263 confirming that clone Tter07B12 encoded a Family 16 endoglucanase.

The cDNA sequence (SEQ ID NO: 3) and deduced amino acid sequence (SEQ ID NO: 4) are shown in FIG. 2. The cDNA clone encodes a polypeptide of 285 amino acids. The % G+C content of the full-length coding region is 68.4% and of the mature protein coding region (nucleotides 55 to 855 of SEQ ID NO: 3) is 68.7%. Using the SignalP software program (Nielsen et al., 1997, supra), a signal peptide of 18 residues was predicted. The predicted mature protein contains 267 amino acids with a molecular mass of 28.2 kDa.

A comparative pairwise global alignment of amino acid sequences was determined using the Clustal W method (Higgins, 1989, supra) with the AlignX module of Vector NTI Advance 10.3 software (Invitrogen, Carlsbad, Calif., USA) and a blosum62mt2 scoring matrix and the following multiple alignment parameters: K-tuple size 1; best diagonals 5; window size 5; gap penalty 5; gap opening penalty 10; gap extension penalty 0.1. The alignment showed that the deduced mature amino acid sequence of the *Thielavia terrestris* GH16B gene shared 58% identity *Trichoderma harzianum* endo-1,3(4)-beta-glucanase Family 16 sequence (GENESEQP: AAR88406; WO 95/31533).

Figure 4:
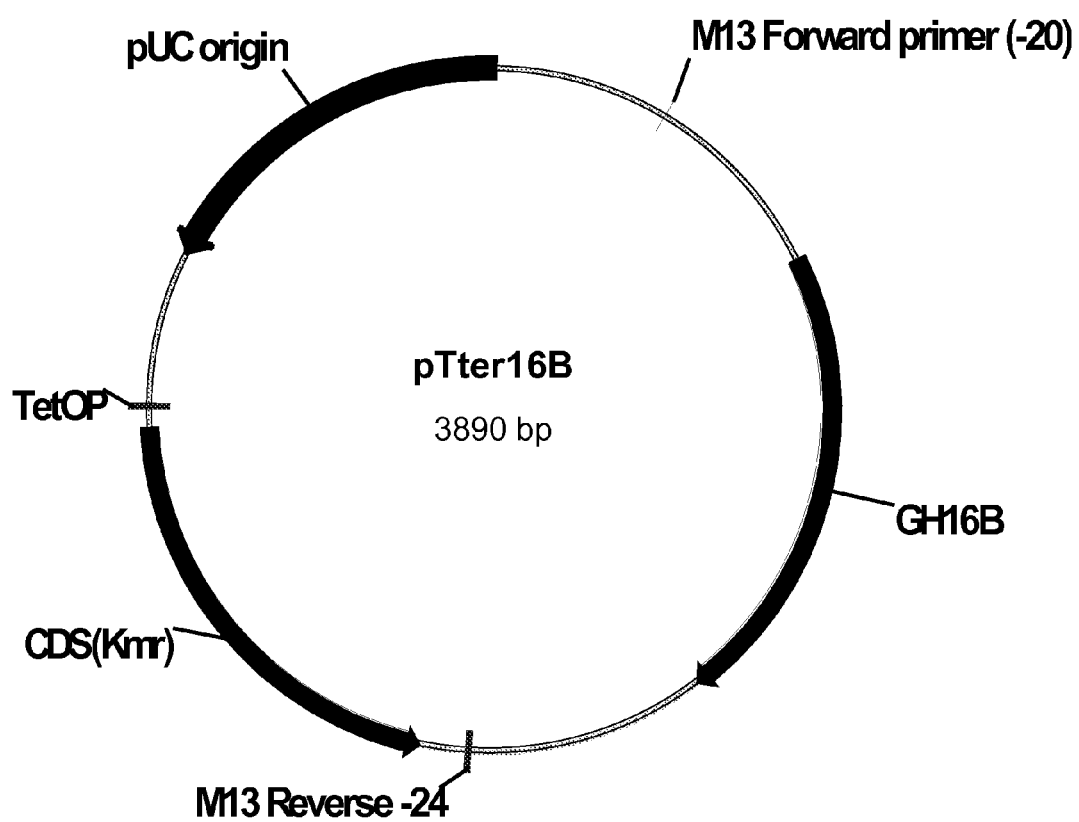
FIG. 4 shows a restriction map of pTter16B.

Once the identities of clones Tter30G12 and Tter07B12 were confirmed, a 0.5 µl aliquot of plasmid DNA from each clone designated pTter16A (FIG. 3) and pTter16B (FIG. 4) was transferred into a separate vial of *E. coli* TOP10 cells (Invitrogen Corp., Carlsbad, Calif., USA), gently mixed, and incubated on ice for 10 minutes. The cells were then heat-shocked at 42° C. for 30 seconds and incubated again on ice for 2 minutes. The cells were resuspended in 250 µl of SOC medium and incubated at 37° C. for 60 minutes with constant shaking at 200 rpm. After the incubation period, two 30 µl aliquots were plated onto LB plates supplemented with 50 µg of kanamycin per ml and incubated overnight at 37° C. The next day a single colony was picked from each transformation and streaked onto three 1.8 ml cryovials containing about 1.5 mls of LB agarose supplemented with 50 µg of kanamycin per ml. The vials were sealed with PETRISEAL™ (Diversified Biotech, Boston Mass., USA) and deposited with the Agricultural Research Service Patent Culture Collection, Northern Regional Research Center, Peoria, Ill., USA, as NRRL B-50081 (pTter16A) and NRRL B-50082 (pTter16B) with a deposit date of Nov. 30, 2007.

DEPOSITS OF BIOLOGICAL MATERIAL

The following biological materials have been deposited under the terms of the Budapest Treaty with the Agricultural Research Service Patent Culture Collection (NRRL), Northern Regional Research Center, 1815 University Street, Peoria, Ill., USA, and given the following accession numbers:

| Deposit | Accession Number | Date of Deposit |
|---|---|---|
| *E. coli* pTter16A | NRRL B-50081 | Nov. 30, 2007 |
| *E. coli* pTter16B | NRRL B-50082 | Nov. 30, 2007 |

The strains have been deposited under conditions that assure that access to the cultures will be available during the pendency of this patent application to one determined by foreign patent laws to be entitled thereto. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a polypeptide having endoglucanase activity, wherein the polynucleotide is operably linked to one or more heterologous control sequences that direct production of the polypeptide in an expression host, and wherein the polypeptide is selected from:
   (a) a polypeptide comprising an amino acid sequence having at least 90% sequence identity to the mature polypeptide of SEQ ID NO: 4;
   (b) a polypeptide encoded by a polynucleotide which hybridizes under at least high stringency conditions with (i) the mature polypeptide coding sequence of SEQ ID NO: 3, (ii) the genomic DNA sequence of the mature polypeptide coding sequence of SEQ ID NO: 3, or (iii) the full-length complement of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.; and
   (c) a polypeptide encoded by a polynucleotide comprising a nucleotide sequence having at least 90% sequence identity to the mature polypeptide coding sequence of SEQ ID NO: 3.

2. The nucleic acid construct of claim 1, wherein the polypeptide having endoglucanase activity comprises an amino acid sequence having at least 90% sequence identity to the mature polypeptide of SEQ ID NO: 4.

3. The nucleic acid construct of claim 1, wherein the polypeptide having endoglucanase activity comprises an amino acid sequence having at least 95% sequence identity to the mature polypeptide of SEQ ID NO: 4.

4. The nucleic acid construct of claim 1, wherein the polypeptide having endoglucanase activity comprises an amino acid sequence having at least 97% sequence identity to the mature polypeptide of SEQ ID NO: 4.

5. The nucleic acid construct of claim 1, wherein the polypeptide having endoglucanase activity is encoded by a polynucleotide which hybridizes under at least high stringency conditions with (i) the mature polypeptide coding sequence of SEQ ID NO: 3, (ii) the genomic DNA sequence of the mature polypeptide coding sequence of SEQ ID NO: 3, or (iii) the full-length complement of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.

6. The nucleic acid construct of claim 1, wherein the polypeptide having endoglucanase activity is encoded by a polynucleotide which hybridizes under at least very high stringency conditions with (i) the mature polypeptide coding sequence of SEQ ID NO: 3, (ii) the genomic DNA sequence of the mature polypeptide coding sequence of SEQ ID NO: 3, or (iii) the full-length complement of (i) or (ii), wherein very high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.

7. The nucleic acid construct of claim 1, wherein the polypeptide having endoglucanase activity is encoded by a polynucleotide which comprises a nucleotide sequence having at least 90% sequence identity to the mature polypeptide coding sequence of SEQ ID NO: 3.

8. The nucleic acid construct of claim 1, wherein the polypeptide having endoglucanase activity is encoded by a polynucleotide which comprises a nucleotide sequence having at least 95% sequence identity to the mature polypeptide coding sequence of SEQ ID NO: 3.

9. The nucleic acid construct of claim 1, wherein the polypeptide having endoglucanase activity is encoded by a polynucleotide which comprises a nucleotide sequence having at least 97% sequence identity to the mature polypeptide coding sequence of SEQ ID NO: 3.

10. The nucleic acid construct of claim 1, wherein the polypeptide having endoglucanase activity comprises or consists of the amino acid sequence of SEQ ID NO: 4, or a fragment thereof having endoglucanase activity.

11. The nucleic acid construct of claim 1, wherein the polypeptide having endoglucanase activity comprises or consists of the mature polypeptide of SEQ ID NO: 4.

12. The nucleic acid construct of claim 1, wherein the polypeptide having endoglucanase activity is encoded by a polynucleotide which comprises or consists of the nucleotide sequence of SEQ ID NO: 3; or a subsequence thereof encoding a polypeptide fragment having endoglucanase activity.

13. The nucleic acid construct of claim 1, wherein the polypeptide having endoglucanase activity is encoded by a polynucleotide which is contained in plasmid pTter16B which is contained in *E. coli* NRRL B-50082.

14. A recombinant expression vector comprising the nucleic acid construct of claim 1.

15. An isolated recombinant host cell comprising the nucleic acid construct of claim 1.

16. A method for producing a polypeptide having endoglucanase activity, comprising: (a) cultivating the recombinant host cell of claim 15 under conditions conducive for production of the polypeptide; and (b) recovering the polypeptide.

17. A method for producing a polypeptide having endoglucanase activity, comprising: (a) cultivating a transgenic plant or a plant cell comprising the polynucleotide of claim 1 under conditions conducive for production of the polypeptide; and (b) recovering the polypeptide.

18. A transgenic plant, plant part or plant cell, which has been transformed with the nucleic acid construct of claim 1.

19. The nucleic acid construct of claim 1, wherein the polypeptide having endoglucanase activity is a variant comprising a substitution, deletion, or insertion of one or more amino acids of the mature polypeptide of SEQ ID NO: 4.

20. The nucleic acid construct of claim 1, wherein the polypeptide having endoglucanase activity comprises an amino acid sequence having at least 99% sequence identity to the mature polypeptide of SEQ ID NO: 4.

* * * * *